US00PP29472P3

(12) United States Plant Patent
Head

(10) Patent No.: US PP29,472 P3
(45) Date of Patent: Jul. 10, 2018

(54) ***METASEQUOIA* PLANT NAMED 'WAH-08AG'**

(50) Latin Name: *Metasequoia glyptostroboides*
Varietal Denomination: WAH-08AG

(71) Applicant: William A. Head, Seneca, SC (US)

(72) Inventor: William A. Head, Seneca, SC (US)

(73) Assignee: Southern Plant Group, Marietta, GA (US)

( * ) Notice: Subject to any disclaimer, the term of this patent is extended or adjusted under 35 U.S.C. 154(b) by 0 days.

(21) Appl. No.: 15/731,148

(22) Filed: Apr. 26, 2017

(65) Prior Publication Data

US 2017/0325372 P1 Nov. 9, 2017

Related U.S. Application Data

(60) Provisional application No. 62/391,639, filed on May 6, 2016.

(51) Int. Cl.
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 7/00
See application file for complete search history.

*Primary Examiner* — Kent L Bell
(74) *Attorney, Agent, or Firm* — Audrey Charles

(57) ABSTRACT

A new and distinct cultivar of *Metasequoia* plant named 'WAH-08AG', characterized by its bright yellow-green colored foliage that transitions to greyed-orange in the fall, foliage that resists burning with increased temperature and sunlight, and moderately vigorous, compact, dense pyramidal growth habit, is disclosed.

1 Drawing Sheet

Latin name of genus and species of plant claimed: *Metasequoia glyptostroboides.*

Variety denomination: 'WAH-08AG'.

BACKGROUND OF THE INVENTION

The present invention relates to a new and distinct cultivar of *Metasequoia* plant botanically known as *Metasequoia glyptostroboides* and hereinafter referred to by the cultivar name 'WAH-08AG'.

The new cultivar originated in a controlled breeding program in Seneca, S.C. during the summer of 2007. The objective of the breeding program was the development of *Metasequoia* cultivars having greater heat and sun tolerance.

The new *Metasequoia* cultivar is the result of open-pollination. The female (seed) parent of the new cultivar is 'Ogon' also known as 'Gold Rush', not patented, characterized by its golden foliage that withstands summer heat and vigorous, open-pyramidal growth habit. The male (pollen) parent of the new cultivar is unknown, but presumed to be 'Sheridan Spire', not patented, characterized by its bright green foliage, with upward pointed limbs and vigorous, narrow-columnar growth habit. The new cultivar was discovered and selected as a single seedling within the progeny of the above stated open-pollination. The plant was selected for its compact form and foliage color in the fall of 2008 in a controlled environment in Seneca, S.C.

Asexual reproduction of the new cultivar by terminal stem cuttings since February 2012 in Seneca, S.C. and West Grove, Pa. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'WAH-08AG' as a new and distinct cultivar of *Metasequoia* plant:

1. Bright yellow-green colored foliage that transitions to greyed-orange in the fall;
2. Foliage that resists burning with increased temperature and sunlight; and
3. Moderately vigorous, compact, dense pyramidal growth habit.

Plants of the new cultivar differ from plants of the female parent primarily in having foliage that is more resistant to burning under high temperature and high sun exposure and in growth habit. Plants of the new cultivar differ from plants of the presumed male parent primarily in foliage color and growth habit.

Of the many commercially available *Metasequoia* cultivars, the most similar in comparison to the new cultivar is also the female parent, *Metasequoia* 'Ogon', also known as 'Gold Rush', not patented. However, in side by side comparisons, plants of the new cultivar differ from plants of 'Ogon' in at least the following characteristics:

1. Plants of the new cultivar have foliage coloration that is more resistant to burning with increased temperature and sunlight than plants of 'Ogon';
2. Plants of the new cultivar have foliage coloration that is different from plants of 'Ogon'; and
3. Plants of the new cultivar have a growth habit that is denser and more compact than plants of 'Ogon'.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs differ slightly from the color values cited in the detailed description, which accurately describes the colors of 'WAH-08AG'. With the exception of FIG. 3, the plants were 21 months old and grown for 11 months in an outdoor nursery in West Grove, Pa.

DETAILED BOTANICAL DESCRIPTION

Figure 1:
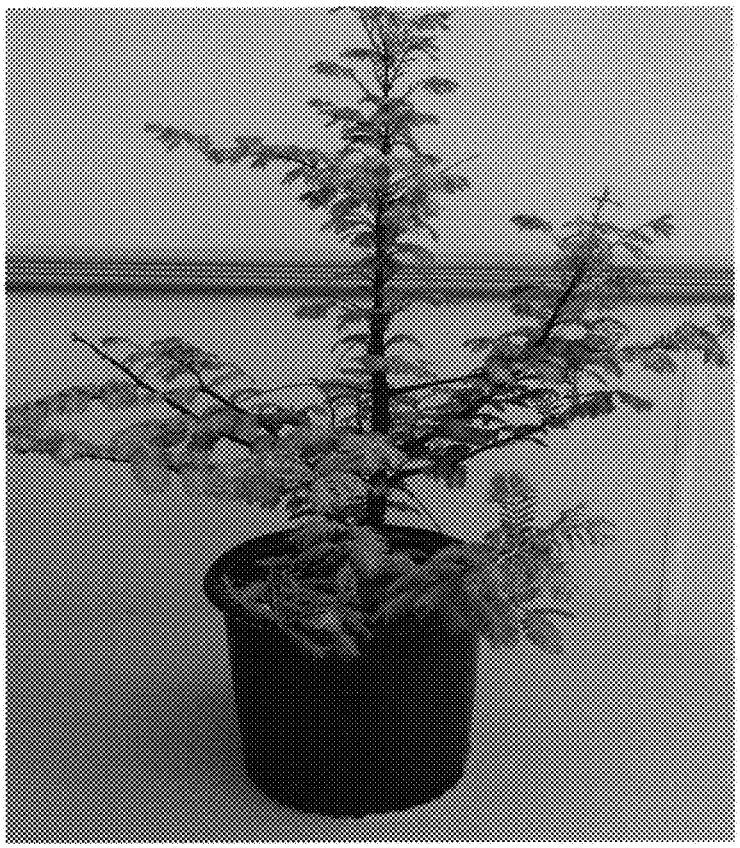
FIG. 1 illustrates a side view of the overall growth of 'WAH-08AG'.
Figure 2:
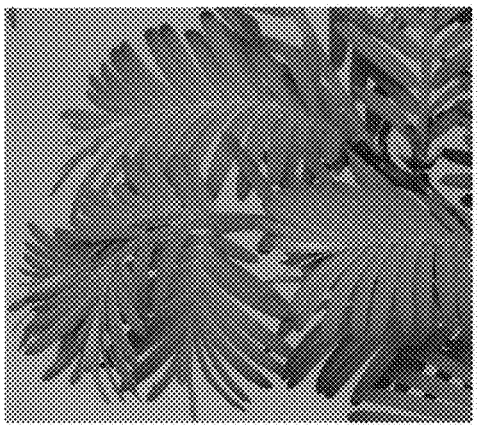
FIG. 2 illustrates a close-up view of the foliage.
Figure 3:
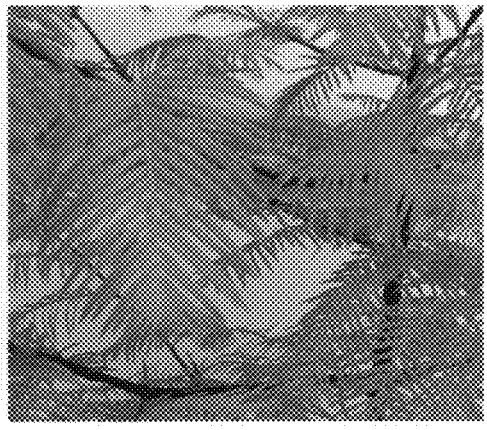
FIG. 3 illustrates a close-up view of the foliage in fall color.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in April 2017 under natural light conditions in West Grove, Pa. Fall color was taken from the same plants in August 2016 under natural light conditions in West Grove, Pa.

The following descriptions and measurements describe plants produced from semi-hardwood cuttings from stock plants and grown outside in a test field in West Grove, Pa. Plants were 21 months old and grown for 11 months in 3 gallon containers utilizing soilless growth medium. Temperatures ranged from an average high of 93.0° F. (33.9° C.) to an average low of 8.0° F. (−13.3° C.). Measurements and numerical values represent averages of typical plants.

Botanical classification: *Metasequoia glyptostoboides* cultivar 'WAH-08AG'.

Parentage:

*Female parent.*—'Ogon' also known as 'Gold Rush', not patented.

*Male parent.*—Unknown, but presumed to be 'Sheridan Spire', not patented.

Propagation:

*Type cutting.*—Semi-hardwood or hardwood; grafting also possible.

*Time to initiate roots in summer.*—10 to 14 days.

*Time to initiate roots in winter.*—30 to 45 days.

*Time to produce a rooted cutting in summer.*—30 to 45 days.

*Time to produce a rooted cutting in winter.*—8.5 to 13 weeks.

*Root description.*—Fleshy, medium thickness. Color: 165C.

*Rooting habit.*—Freely branching, dense.

Plant description:

*Type.*—Deciduous conifer.

*Growth habit and general appearance.*—Moderately vigorous, compact, dense pyramidal form.

*Commercial crop time.*—Approximately 12 months from a rooted cutting to finish in an 3 gallon pot.

*Size.*—Height from soil to top of plant plane: Approximately 63.0 cm. Width: Approximately 63.0 cm. After approximately six years growth plant can reach heights to 4.6 m (15 feet) and widths of 2.0 m to 2.4 m (7 to 8 feet).

*Trunk.*—Diameter at midpoint: Approximately 1.5 cm. Texture: Smooth, glabrous, rough in areas with cracking and exfoliating bark. Color: Between 177A and 174A, with bark of 177A and 200A.

*Branches.*—Freely branching. Strength: Moderately strong. Quantity: Approximately 10 main branches. Appearance: Dull, covered with scale-like leaves. Arrangement: Opposite. Length: Approximately 30.0 cm to 33.0 cm. Diameter: Approximately 4.0 mm. Internode length at midpoint: Approximately 1.3 cm. Texture: Glabrous. Color of young stem: 164A with streaks of 165A. Color of mature stem: 174A with streaks of 201A.

Foliage description:

*General description.*—Type: Approximately 50% compound and 50% simple. Arrangement: Opposite. Quantity per lateral branch: Approximately 12 to 14.

*Leaves.*—Shape: Paripinnate, with an overall oblong shape. Appearance: Dull. Apex: Acute. Base: Attenuate. Margin: Entire. Length: Approximately 3.0 cm to 5.0 cm. Width: Approximately 3.2 cm. Leaflet shape: Ligulate. Leaflet apex: Acute. Leaflet base: Attenuate to Rounded. Leaflet margin: Entire. Leaflet length: Approximately 1.5 cm. Leaflet width: Approximately 2.0 mm. Texture of upper and lower surfaces: Smooth, glabrous. Venation pattern: Parallel. Color of upper surface of young foliage: 144A and N144B with venation indistinguishable from leaf lamina. Color of lower surface of young foliage: 144A and N144B with venation indistinguishable from leaf lamina. Color of upper surface of mature foliage: 144A and N144B, in the fall transitions to a greyed orange 170A through 170C. Color of lower surface of mature foliage: 144B, in the fall transitions to a greyed orange 166D.

*Petiole.*—Length: Approximately 3.0 mm. Diameter: Approximately 2.0 mm. Texture: Smooth, glabrous. Color: N144B.

Cone and seed production: Not available, cone and seed production were not observed.

Disease and pest resistance: Plants of the new *Metasequoia* have not been noted to be resistant to pathogens and pests common to *Metasequoia*.

Weather tolerance: Plants of the new *Metasequoia* have been observed to tolerate high temperatures of about 40° C. (104° F.) and low temperatures of about −16° C. (3.2° F.).

What is claimed is:

1. A new and distinct cultivar of *Metasequoia* plant named 'WAH-08AG', substantially as herein illustrated and described.

* * * * *